(12) United States Patent
Ma et al.

(10) Patent No.: US 7,553,896 B2
(45) Date of Patent: Jun. 30, 2009

(54) ORTHO-NITROSOPHENOLS AS POLYMERIZATION INHIBITORS

(75) Inventors: Qinggao Ma, Naugatuck, CT (US);
William A. Wortman, Harwinton, CT (US); Jay Wang, Naperville, IL (US);
Paul E. Stott, Oxford, CT (US)

(73) Assignee: Chemtura Corporation, Middlebury, CT (US)

( * ) Notice: Subject to any disclaimer, the term of this patent is extended or adjusted under 35 U.S.C. 154(b) by 784 days.

(21) Appl. No.: 11/156,214

(22) Filed: Jun. 17, 2005

(65) Prior Publication Data

US 2006/0283699 A1 Dec. 21, 2006

(51) Int. Cl.
C08K 5/16 (2006.01)

(52) U.S. Cl. .................. 524/186; 524/260; 524/481; 524/866; 526/348

(58) Field of Classification Search .......... 524/186, 524/260, 481, 866; 526/348
See application file for complete search history.

(56) References Cited

U.S. PATENT DOCUMENTS

| 3,163,677 | A |   | 12/1964 | Hoffman | 260/583 |
|---|---|---|---|---|---|
| 3,267,132 | A |   | 8/1966 | Newsom | 260/465.9 |
| 3,988,212 | A |   | 10/1976 | Watson | 203/9 |
| 4,003,800 | A |   | 1/1977 | Bacha et al. | 203/9 |
| 4,040,911 | A |   | 8/1977 | Bacha et al. | 203/9 |
| 4,086,147 | A |   | 4/1978 | Watson | 203/9 |
| 4,105,506 | A |   | 8/1978 | Watson | 203/9 |
| 4,132,602 | A |   | 1/1979 | Watson | 203/9 |
| 4,132,603 | A |   | 1/1979 | Watson | 203/9 |
| 4,182,658 | A |   | 1/1980 | Watson | 203/9 |
| 4,252,615 | A |   | 2/1981 | Watson | 203/9 |
| 4,341,600 | A |   | 7/1982 | Watson | 203/9 |
| 4,466,904 | A |   | 8/1984 | Watson et al. | 252/402 |
| 4,468,343 | A |   | 8/1984 | Butler et al. | 252/403 |
| 5,254,760 | A |   | 10/1993 | Winter et al. | 585/5 |
| 5,468,789 | A | * | 11/1995 | Lewis et al. | 524/99 |
| 5,504,243 | A |   | 4/1996 | Sakamoto et al. | 560/205 |
| 5,545,782 | A |   | 8/1996 | Winter et al. | 585/5 |
| 5,545,786 | A |   | 8/1996 | Winter et al. | 585/435 |
| 5,583,247 | A |   | 12/1996 | Nesvadba et al. | 560/2 |
| 5,616,774 | A |   | 4/1997 | Evans et al. | 560/4 |
| 5,670,692 | A |   | 9/1997 | Nesvadba et al. | 558/71 |
| 5,750,765 | A |   | 5/1998 | Nesvadba et al. | 560/126 |
| 5,888,356 | A |   | 3/1999 | Keil et al. | 203/8 |
| 5,910,232 | A |   | 6/1999 | Hyde et al. | 203/9 |
| 6,342,647 | B1 |   | 1/2002 | Roof et al. | 585/5 |
| 6,395,943 | B1 |   | 5/2002 | Kurek et al. | 585/5 |
| 6,685,823 | B2 |   | 2/2004 | Benage et al. | 208/48 |
| 7,125,475 | B2 | * | 10/2006 | Benage | 203/8 |

FOREIGN PATENT DOCUMENTS

| EP | 0 020 065 | * | 12/1980 |
|---|---|---|---|
| EP | 0178168 |   | 4/1986 |
| EP | 0240297 |   | 10/1987 |
| EP | 0765856 A1 |   | 4/1997 |
| FR | 2761060 |   | 9/1998 |
| HU | 150550 |   | 9/1961 |
| JP | 56045970 |   | 4/1981 |
| JP | 2003277302 |   | 10/2003 |
| JP | 2003277423 |   | 10/2003 |
| SU | 478838 |   | 3/1976 |
| WO | 98/14416 |   | 4/1998 |
| WO | 98/25872 |   | 6/1998 |
| WO | 99/20584 |   | 4/1999 |
| WO | WO99/21893 |   | 5/1999 |
| WO | WO03/070687 A1 |   | 8/2003 |

OTHER PUBLICATIONS

Journal of Applied Polymer Science., Relative inhibitory effect of various compounds on the rate of polymerization of methyl methaerylate, vol. 9, pp. 2009-2018 (1965).
The Royal Society of Chemistry, Acceleration in nitroxide mediated living free radical polymerizations, pp. 823-824m (2001).

* cited by examiner

*Primary Examiner*—Ling-Siu Choi
(74) *Attorney, Agent, or Firm*—Jaimes Sher

(57) ABSTRACT

Disclosed herein is a method for inhibiting the premature polymerization of ethylenically unsaturated monomers comprising adding to said monomers an effective amount of at least one nitroso inhibitor of the structure:

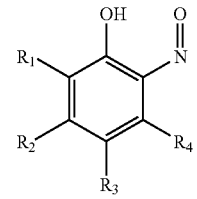

wherein $R_1$, $R_2$, $R_3$, and $R_4$ are independently selected from the group consisting of hydrogen, nitro, nitroso, halogen, COOR wherein R is hydrogen or alkyl, alkyl, and heteroatom-substituted alkyl; or adjacent groups $R_1$, $R_2$, $R_3$, and $R_4$ can be taken together to form a substituted or unsubstituted fused six-membered ring.

Also disclosed is a composition of matter comprising:
A) an ethylenically unsaturated monomer and
B) at least one nitroso compound of the above-described structure.

8 Claims, No Drawings

ORTHO-NITROSOPHENOLS AS POLYMERIZATION INHIBITORS

BACKGROUND OF THE INVENTION

1. Field of the Invention

The present invention is directed to the use of at least one o-nitrosophenol compound, alone or in combination with at least one stable nitroxide free radical compound, and/or at least one nitroaromatic compound, and/or at least one quinone alkide compound, preferably a quinone methide, and/or at least one quinone compound, and/or at least one hydroquinone compound, and/or at least one hydroxylamine compound, and/or at least one phenylenediamine compound, and/or air or oxygen to inhibit the polymerization of ethylenically unsaturated monomers.

2. Description of Related Art

Many ethylenically unsaturated monomers undesirably polymerize at various stages of their manufacture, processing, handling, storage, and use. A particularly troublesome problem is equipment fouling caused by polymerization in the purification stages of the production processes of such monomers. Polymerization, such as thermal polymerization, during their purification results in the loss of monomer and a loss in production efficiency owing to the deposition of polymer in or on the equipment being used in the purification, the deposits of which must be removed from time to time. Additionally, the formation of soluble polymer leads to loss of monomer, i.e., a lower yield, and an increase in the viscosity of any tars that may be produced. The processing of the tars then requires higher temperature and work (energy cost) to remove residual monomer.

A wide variety of compounds has been proposed and used for inhibiting uncontrolled and undesired polymerization of ethylenically unsaturated monomers. There remains a need, however, for an inhibitor that not only provides highly effective inhibition of polymerization during normal operation of a continuous manufacturing or purification process, but also provides satisfactory protection in the event of a loss of continuous inhibitor feed. While many inhibitors are known to provide sufficient protection in one of these scenarios, they have not been fully satisfactory under both normal and upset operating conditions. Accordingly, a substantial need continues in the art for improved compositions for inhibiting the polymerization of such monomers during their production and during the distillation process for purifying or separating them from impurities, as well as during transport and storage.

N-nitroso compounds and C-nitrosophenols are known as polymerization inhibitors, especially under the conditions for monomer production and processing.

Aromatic nitroso and di-nitroso compounds are also known to be useful as chemical agents capable of promoting the formation of filler-elastomer linkages. The aromatic nitroso compounds may be aromatic amines, including polyamines or phenolic compounds. They are also known to be useful intermediates in the production of other chemicals, such as p-aminodiphenylamine.

U.S. Pat. No. 3,163,677 discloses N,N,O-trisubstituted hydroxylamines and N,N-disubstituted nitroxides of the formulas:

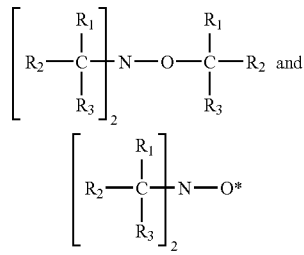

wherein $R_1$, $R_2$, and $R_3$ are each an alkyl radical having 1 to 15 carbon atoms. (As used herein, the designation N—O* denotes a stable free radical wherein the asterisk is an unpaired electron.) The N,N,O-trisubstituted hydroxylamines can be used to make the N,N-disubstituted nitroxides, which are stable free radicals and are said to be useful as polymerization inhibitors.

U.S. Pat. No. 3,267,132 discloses that the polymerization of unsaturated nitriles can be greatly inhibited by incorporating therein a minor amount of a nitroso compound selected from the group consisting of p-nitrosodiarylamines and N-nitrosoarylamines.

U.S. Pat. Nos. 3,988,212 and 4,341,600 disclose the use of N-nitrosodiphenylamine combined with dinitro-cresol derivatives for inhibiting the polymerization of vinyl aromatic compounds under vacuum distillation conditions.

U.S. Pat. Nos. 4,003,800 and 4,040,911 disclose the use of quinone alkides in a styrene purification process.

U.S. Pat. No. 4,086,147 discloses a process using 2-nitro-p-cresol as a polymerization inhibitor.

U.S. Pat. Nos. 4,105,506 and 4,252,615 disclose a process using 2,6-dinitro-p-cresol as a polymerization inhibitor.

U.S. Pat. Nos. 4,132,602 and 4,132,603 disclose the use of a halogenated aromatic nitro compound as a polymerization inhibitor for use during the distillation of vinyl aromatic compounds.

U.S. Pat. No. 4,182,658 discloses a method for preventing the polymerization of a readily polymerizable vinyl aromatic compound during distillation at elevated temperatures within a distillation apparatus that is subject to an emergency condition, such as a power outage. This method comprises force-feeding a supplemental polymerization inhibitor having a high solubility in the vinyl aromatic compound and a long duration of efficiency into each of the distillation vessels of a conventional distillation apparatus in an amount sufficient to prevent polymerization therein.

U.S. Pat. No. 4,252,615 discloses a process for the distillation of readily polymerizable vinyl aromatic compounds and a polymerization inhibitor therefor. The process comprises subjecting a vinyl aromatic compound to elevated temperatures in a distillation system in the presence of a polymerization inhibitor comprising 2,6-dinitro-p-cresol.

U.S. Pat. No. 4,341,600 discloses a process for distilling vinyltoluene comprising subjecting vinyltoluene to distillation conditions in the presence of a synergistic polymerization inhibiting mixture of N-nitrosodiphenylamine (NDPA) and dinitro-para-cresol (DNPC). Preferably from about 100 to about 300 ppm by weight NDPA and about 300 to about 700 ppm by weight DNPC are dissolved in the crude vinyltoluene and the resulting solution is vacuum distilled.

U.S. Pat. No. 4,466,904 discloses the use of phenothiazine, 4-tert-butylcatechol and 2,6-dinitro-p-cresol as a polymerization inhibitor system in the presence of oxygen during heating of vinyl aromatic compounds.

U.S. Pat. No. 4,468,343 discloses a composition and a process for utilizing 2,6-dinitro-p-cresol and either a phenylenediamine or 4-tert-butylcatechol in the presence of oxygen to prevent the polymerization of vinyl aromatic compounds during heating.

U.S. Pat. No. 5,254,760 teaches that the polymerization of a vinyl aromatic compound, such as styrene, is very effectively inhibited during distillation or purification by the presence of at least one stable nitroxyl compound together with at least one aromatic nitro compound.

U.S. Pat. No. 5,504,243 discloses a method for inhibiting polymerizable (meth)acrylic acid and esters thereof from polymerizing during their production, transportation and storage by using as the inhibitor N-oxyl compound and more than one compound selected from the group consisting of manganese salt compound, copper salt compound, 2,2,6,6,-tetramethylpiperidine compound and nitroso compound. The N-oxyl compound is one or more kinds selected from 2,2,6,6,-tetramethylpiperidinooxyl, 4-hydroxy-2,2,6,6,-tetramethylpiperidinooxyl and 4,4',4"-tris-(2,2,6,6,-tetramethylpiperidinooxyl)phosphite. The combined use of the inhibitors is said to provide a superior inhibiting effect to use alone.

U.S. Pat. Nos. 5,545,782 and 5,545,786 disclose that nitroxyl inhibitors in combination with some oxygen reduce the premature polymerization of vinyl aromatic monomers during the manufacturing processes for such monomers. Even small quantities of air used in combination with the nitroxyl inhibitors are said to result in vastly prolonged inhibition times for the monomers.

U.S. Pat. Nos. 5,583,247, 5,670,692, and 5,750,765 disclose the protection of ethylenically unsaturated monomers from premature polymerization during manufacture and storage by the incorporation therein of an effective stabilizing amount of a quinone methide compound having an electron withdrawing substituent at the 7-methylene group.

U.S. Pat. No. 5,616,774 discloses the protection of ethylenically unsaturated monomers from premature polymerization during manufacture and storage by the incorporation therein of an effective stabilizing amount of a 7-aryl quinone methide compound wherein the 7-aryl substituent is 2-, 3-, or 4-pyridyl, 2- or 3-thienyl, 2- or 3-pyrryl, 2- or 3-furyl, aryl of six to 10 carbon atoms, or said aryl substituted by one to three alkyl of one to eight carbon atoms, alkoxy of one to eight carbon atoms, alkylthio of one to eight carbon atoms, alkylamino of one to eight carbon atoms, dialkylamino of two to eight carbon atoms, alkoxycarbonyl of two to eight carbon atoms, hydroxy, nitro, amino, cyano, carboxy, aminocarbonyl, chloro, or mixtures of said substituents. The combination of these quinone methides with at least one stable nitroxyl compound is also disclosed.

U.S. Pat. No. 5,888,356 discloses inhibiting the polymerization of a vinylaromatic or vinylaliphatic compound at elevated temperature in the absence of air by processing the vinylaromatic or vinylaliphatic compound in the presence of 4-hydroxy-2,2,6,6-tetramethylpiperidine-N-oxyl or 4-acetylamino-2,2,6,6-tetramethylpiperidine-N-oxylalone or in admixture with p-nitrosophenol or 2-methyl-4-nitrosophenol.

U.S. Pat. No. 5,910,232 teaches that inhibition performance in styrene processing is improved through the addition of a stable nitroxide free radical compound to the styrene feed and to the reflux of at least one column. A nontoxic retarder, such as phenylenediamine, may also optionally be added to the styrene feed and to the reflux.

U.S. Pat. No. 6,342,647 discloses that the polymerization of vinyl aromatic compounds, such as styrene, may be inhibited by the addition of a composition that contains a hindered hydroxylamine, and, optionally, a synergist together with the hindered hydroxylamine. In one embodiment of the invention, the hindered N,N-disubstituted hydroxylamine has the formula: $[(R^1\ R^2\ R^3)C]_2N-OH$ where $R^1$, $R^2$, and $R^3$ are independently selected from the group consisting of hydrogen, straight, branched or cyclic alkyl, aryl, aralkyl, and alkaryl moieties; where no more than two of $R^1$, $R^2$, and $R^3$ on each C can be hydrogen at a time; where one or more of $R^1$, $R^2$, and $R^3$ on one C may be joined to an $R^1$, $R^2$, and $R^3$ on the other C to form a cyclic moiety selected from the group consisting of alkylene, and aralkylene moieties; where any two of the $R^1$, $R^2$, and $R^3$ on any one C may be joined together to form a cycloalkyl; where any of the above definitions of $R^1$, $R^2$, and $R^3$ may contain one or more heteroatoms selected from the group consisting of N, O and S; and where the total number of carbon atoms in the hindered N,N-disubstituted hydroxylamine ranges from 6 to 70. Optional synergists may include alkyl-substituted hydroxyarenes such as 2,5-di-tert-butylhydroquinone, and hydrogen transfer agents such as 1,2,3,4-tetrahydronaphthalene; and the like, and mixtures thereof.

U.S. Pat. No. 6,395,943 discloses a process for inhibiting the polymerization of vinyl aromatic compounds, such as styrene, during its distillation. The process involves adding a mixture of at least two inhibitors to the vinyl aromatic compound. One such combination is N,N'-di-2-butyl-N,N',4-dinitroso-1,4-diaminobenzene and dinitrocresol. A stabilizer such as N,N'-di-2-butyl-1,4-diaminobenzene can also be added.

U.S. Pat. No. 6,685,823 discloses a method for inhibiting the premature polymerization of ethylenically unsaturated monomers comprising adding to said monomers an effective amount of at least one inhibitor selected from the group consisting of C-nitrosoaniline and quinone imine oxime compounds. Also disclosed is a composition of matter comprising: A) an ethylenically unsaturated monomer and B) an effective inhibiting amount, sufficient to prevent premature polymerization during distillation or purification of said ethylenically unsaturated monomer, of at least one inhibitor selected from the group consisting of C-nitrosoaniline and quinone imine oxime compounds used together with an effective amount of oxygen or air to enhance the inhibiting activity of said inhibitor.

European Patent Application 0 178 168 A2 discloses a method for inhibiting the polymerization of an ($\alpha,\beta$-ethylenically unsaturated monocarboxylic acid during its recovery by distillation by using a nitroxide free radical.

European patent application 240,297 A1 teaches the use of a substituted hydroxylamine and a dinitrophenol to inhibit the polymerization of a vinyl aromatic compound at elevated temperatures in a distillation process.

European Patent Application 0 765 856 A1 discloses a stabilized acrylic acid composition in which the polymerization of the acrylic acid is inhibited during the distillation process for purifying or separating the acrylic acid as well as during transport and storage. The compositions comprise three components: (a) acrylic acid, (b) a stable nitroxyl radical, and (c) a dihetero-substituted benzene compound having at least one transferable hydrogen (e.g., a quinone derivative such as the monomethyl ether of hydroquinone (MEHQ)). During the distillation process, transport, and storage, components (b) and (c) are present in a polymerization-inhibiting amount. During the distillation process, oxygen (d) is preferably added with components (b) and (c).

FR 2,761,060 relates to the prevention of premature polymerization of styrene during its production by dehydrogenation of ethylbenzene by injecting into the process effluent a radical inhibitor based on an oxyl-tetramethylpiperidine derivative.

Hung. 150,550 discloses that free radical polymerization was inhibited with organic nitroso compounds, e.g., p-$H_2NC_6H_4NO$ (I), α-nitroso-β-naphthol, or β-nitroso-α-naphthol. For example, addition of 0.3 grams of (I) to one liter of styrene is said to have resulted in the stability of the latter for months. Also, (I) could be removed with azodiisobutyronitrile.

JP2003277302 discloses that 5 ppm of a 4-hydroxyl TEMPO/95 ppm DBSA blend can inhibit styrene polymerization for ten minutes under certain laboratory test conditions.

JP2003277423 discloses that 5 ppm DBSA/100 ppm DNBP showed a good inhibiting effect.

SU-478838 is directed to the inhibition of the radical polymerization of oligoester acrylates and the prevention of oligomeric peroxides using a binary polymerization inhibitor comprising quinone.

WO 98/14416 discloses that the polymerization of vinyl aromatic monomers such as styrene is inhibited by the addition of a composition of a stable hindered nitroxyl radical and an oxime compound.

WO 98/25872 concerns substance mixtures containing: (A) compounds containing vinyl groups; (B) an active amount of a mixture which inhibits premature polymerization of the compounds containing vinyl groups and contains: (i) at least one N-oxyl compound of a secondary amine which does not carry any hydrogen atoms on the α-carbon atoms; and (ii) at least one iron compound; (C) optionally nitro compounds; and (D) optionally co-stabilizers. The publication also discloses a process for inhibiting the premature polymerization of compounds (A) containing vinyl groups, and the use of (B) optionally mixed with nitro compounds (C) and/or co-stabilizers (D) for inhibiting the premature polymerization of radically polymerizable compounds and stabilizing organic materials against the harmful effect of radicals.

WO 99/20584 discloses that polymerization can be inhibited during the anaerobic production of styrene through the addition of a combination of a stable nitroxide free radical compound and a nontoxic phenylenediamine compound.

Georgieff, K. K., *J Appl. Polymer Sci.* 9(6):2009-18 (1965) measured the inhibitory effect of the following compounds on the bulk polymerization of methyl methacrylate: hydroquinone, p-tert-butylcatechol, p-methoxyphenol, 2,4-dichloro-6-nitrophenol, n-propyl gallate, di-tert-butyl-p-cresol, 2,2'-methylenebis(4-methyl-6-tert-butylphenol), 1-amino-7-naphthol, p-benzoquinone, 2,6-dichloro-p-benzoquinone, 2-amino-1,4-naphthoquinone, three aminoanthraquinones, diphenylamine, p-nitrosodimethylaniline, α- and β-naphthylamine, phenothiazine, N-nitroso-dimethylamine, hexamethylphosphoramide, n-dodecyl mercaptan, benzenethiol, 2,2-diphenyl-1-picrylhydrazyl, phenyl hydrazine, divinylacetylene, and various antimony and copper salts. Polymerization was carried out in a test tube in a bath at 101.2° C., benzoyl peroxide being used as initiator. Generally, phenols and naphthols were the strongest inhibitors, followed by quinones, aromatic amines, 2,2-diphenyl-1-picrylhydrazyl, antimony pentachloride, phenyl hydrazine, divinylacetylene, and the thiols.

Harth, E. et al., *Chem. Commun.* 9:823-824 (2001) reported that intramolecular H-bonding is a powerful tool in increasing the performance of alkoxylamine initiators for nitroxide mediated living free radical polymerizations.

The foregoing are incorporated herein by reference in their entirety.

SUMMARY OF THE INVENTION

It is well known that vinyl compounds, such as styrene and acrylates, have a strong tendency to polymerize under elevated temperatures. This polymerization is undesirable during their manufacture, processing, handling, storage, and use. A particular problem during the monomer purification process, usually through continuous vacuum distillation, the formation of soluble polymer leads to loss of monomer, i.e., a lower yield, and an increase in the viscosity of any tars that may be produced, and a loss in production efficiency owing to the deposition of polymer in or on the equipment being used in the purification, the deposits of which must be removed from time to time, and an exothermic and uncontrollable polymerization during a plant upset when no fresh inhibitor could be added may lead to disastrous results.

A wide variety of compounds has been proposed and used for inhibiting uncontrolled and undesired polymerization of ethylenically unsaturated monomers under different conditions. Many compounds that are effective for inhibiting the polymerization of vinyl aromatic compounds under storage conditions, such as alkylphenol or hydroquinones, are not suitable for a vacuum distillation process, since they are effective only in the presence of oxygen. The partial pressure of oxygen in a vacuum distillation column is accordingly too low for these storage inhibitors to be effective.

For the compounds that are effective for a continuous distillation process, the ideal inhibitor should work both with air and without air. Currently, these inhibitors are categorized into two classes: "true inhibitors" and "retarders". The so-called "true inhibitors" ensure the low production of undesirable polymers under normal operation conditions; however, during a plant upset, when no fresh "true inhibitors" can be added, the leftover inhibitors are quickly consumed and the polymerization may go out of control. These "true inhibitors" include nitroxides, aromatic nitroso compound, (non ortho) nitrosophenols, N-nitroso aromatics, and the like. "Retarders" on the other hand, allow more polymer to form during normal operation, which leads to relatively low monomer production, but during plant upsets, "retarders" are thought to be able to protect the column for a long period of time. Aromatic nitrophenols are considered to be such compounds. Previously known distillation inhibitors do not have both the characters of "true inhibitor" and "retarder" and are not fully satisfactory.

Physical blends of "true inhibitors" and "retarders" seemingly solved the problem. For example, commercially available blends of 100 ppm nitroxide and 150 ppm DNBP blends are commonly used, but, in fact, they do not offer long enough protection during a serious plant upset. The "true inhibitor" gets consumed quickly during a plant upset and the amount of DNBP "retarder" left in the physical blend, which in this case is significantly less than when retarder itself is used alone, is not enough to handle the situation. Therefore, the polymerization can run out of control much more quickly, since the blend can not provide a sufficiently long protection time for the plant.

The present invention is directed to the use of at least one compound having both true inhibitor and retarder characteristics, alone or in combination with at least one additional inhibitor, in the presence or absence of air or oxygen, to prevent or retard the polymerization of ethylenically unsaturated monomers.

More particularly, the present invention is directed to a method for inhibiting the premature polymerization of ethylenically unsaturated monomers comprising adding to said monomers an effective amount of at least one nitroso inhibitor of the structure:

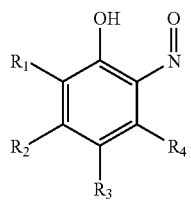

wherein $R_1$, $R_2$, $R_3$, and $R_4$ are independently selected from the group consisting of hydrogen, nitro, nitroso, halogen, COOR wherein R is hydrogen or alkyl, alkyl, and heteroatom-substituted alkyl; or adjacent groups $R_1$, $R_2$, $R_3$, and $R_4$, i.e., $R_1$ and $R_2$, or $R_2$ and $R_3$, or $R_3$ and $R_4$, can be taken together to form a substituted or unsubstituted fused six-membered ring. For convenience, compounds having this structure are referred to herein simply as ortho-nitrosophenols.

In another aspect, the present invention is directed to a composition of matter comprising:

A) an ethylenically unsaturated monomer and

B) an effective inhibiting amount, sufficient to prevent premature polymerization during distillation or purification of said ethylenically unsaturated monomer, of at least one nitroso compound of the structure:

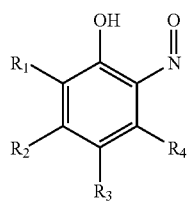

wherein $R_1$, $R_2$, $R_3$, and $R_4$ are independently selected from the group consisting of hydrogen, nitro, nitroso, halogen, COOR wherein R is hydrogen or alkyl, alkyl, and heteroatom-substituted alkyl; or adjacent groups $R_1$, $R_2$, $R_3$, and $R_4$ can be taken together to form a substituted or unsubstituted fused six-membered ring.

Preferably, the nitroso compound is a substituted or unsubstituted ortho-nitrosophenol or a substituted or unsubstituted ortho-nitrosophenol.

DESCRIPTION OF THE PREFERRED EMBODIMENTS

The nitroso compounds of the present invention, which are commercially available, can be used alone or in combination with at least one nitroxyl compound, at least one nitroaromatic compound, at least one quinone alkide, at least one quinone derivative, at least one hydroquinone derivative, at least one hydroxylamine compound, at least one phenylenediamine compound, air or oxygen, or a mixture of the foregoing.

These compounds are suitable for use over a wide range of temperatures, but distillation temperatures employed with the ethylenically unsaturated monomers that are stabilized by the process of the present invention typically range from about 60° C. to about 180° C., preferably from about 70° C. to about 165° C. and, more preferably, from about 80° C. to about 150° C. Such distillations are generally performed at an absolute pressure in the range of about 10 to about 1,200 mm of Hg.

As noted above, the nitroso compounds employed in the practice of the present invention are of the structure:

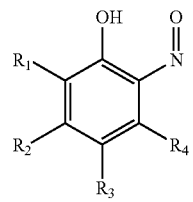

wherein $R_1$, $R_2$, $R_3$, and $R_4$ are independently selected from the group consisting of hydrogen, nitro, nitroso, halogen, alkyl, heteroatom-substituted alkyl, and COOR wherein R is hydrogen or alkyl; or adjacent groups $R_1$, $R_2$, $R_3$, and $R_4$, i.e., $R_1$ and $R_2$, or $R_2$ and $R_3$, or $R_3$ and $R_4$, can be taken together to form a substituted or unsubstituted fused six-membered ring.

Where any of R, $R_1$, $R_2$, $R_3$, or $R_4$ are alkyl, they are preferably alkyl of from 1 to about 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, isomers of the foregoing, and mixtures thereof. Similarly, where any of $R_1$, $R_2$, $R_3$, or $R_4$ are heteroatom-substituted alkyl, the alkyl moiety thereof preferably comprises from 1 to about 15 carbon atoms. Preferably the heteroatom(s) of such heteroatom-substituted alkyls will be selected from the group consisting of oxygen, sulfur, nitrogen, and combinations thereof.

Where a nitroso compound of the present invention comprises a substituted fused six-membered ring, the substituent(s) on such ring can be any that will not adversely affect the true inhibitor and retarder characteristics of the compound as a whole in a significant way.

Most preferably, the nitroso compound employed in the practice of the present invention is selected from the group consisting of 2-nitroso-naphthol, 1-nitroso-2-naphthol, and mixtures thereof.

The nitroxyl compounds that can be employed in combination with the nitroso compounds employed in the practice of the present invention are preferably of the structure:

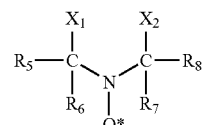

wherein $R_5$ and $R_8$ are independently selected from the group consisting of hydrogen, alkyl, and heteroatom-substituted alkyl and $R_6$ and $R_7$ are (1) independently selected from the group consisting of alkyl and heteroatom-substituted alkyl, or (2) taken together, form a ring structure with the nitrogen; and $X_1$ and $X_2$ (1) are independently selected from the group consisting of halogen, phosphorus (in any of its oxidation states), cyano, $COOR_9$, —S—$COR_9$, —$OCOR_9$, (wherein $R_9$ is alkyl or aryl), amido, —S—$C_6H_5$, carbonyl, alkenyl, or alkyl of 1 to 15 carbon atoms, or (2) taken together, form a ring structure with the nitrogen.

In a particularly preferred embodiment, the nitroxyl compound has the structural formula:

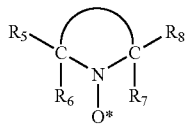

wherein $R_5$ and $R_8$ are independently selected from the group consisting of hydrogen, alkyl, and heteroatom-substituted alkyl and $R_6$ and $R_7$ are independently selected from the group consisting of alkyl and heteroatom-substituted alkyl, and the

portion represents the atoms necessary to form a five-, six-, or seven-membered heterocyclic ring.

The quinone alkide compounds that can be employed in combination with the nitroso compounds in the practice of the present invention are preferably of the structure:

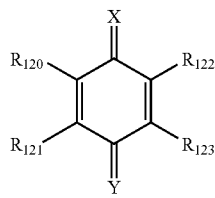

wherein
X is oxygen;
Y is $CR_{124}R_{125}$;
$R_{120}$, $R_{121}$, $R_{122}$, and $R_{123}$ are independently selected from the group consisting of hydrogen, alkyl, aryl, cycloalkyl, sulfonyl, heterocyclic, substituted alkyl, substituted aryl, $OR_{110}$, $NR_{110}R_{111}$, $SR_{110}$, NO, $NO_2$, CN, $COR_{112}$, and halogen, or $R_{120}$ and $R_{121}$ can be taken together and/or $R_{122}$ and $R_{123}$ can be taken together to form one or two ring structures, respectively, either of which can be of five to seven members;

$R_{124}$ and $R_{125}$ are independently selected from the group consisting of hydrogen, alkyl, aryl, cycloalkyl, heterocyclic, substituted alkyl, substituted aryl, $OR_{110}$ $NR_{110}R_{111}$, $SR_{110}$, $NO_2$, NO, CN, $COR_{112}$, halogen, and/or can be taken together to form a ring structure of five to seven members;

$R_{110}$ and $R_{111}$ are independently selected from the group consisting of hydrogen, alkyl, aryl, acyl, benzyl, cyclic, heterocyclic, substituted alkyl or aryl where the substituents are C, O, N, S, or P, and $COR_{102}$, or $R_{110}$ and $R_{111}$ can be taken together to form a ring structure of five to seven members;

$R_{112}$ is $R_{102}$, $OR_{102}$, or $NR_{102}R_{103}$; and $R_{102}$ and $R_{103}$ are independently selected from the group consisting of hydrogen, alkyl, aryl, benzyl, cyclic, heterocyclic, and substituted alkyl or aryl where the substituents are C, O, N, S, or P, or $R_{102}$ and $R_{103}$ can be taken together to form a ring structure of five to seven members.

The nitroaromatic compounds that can be employed in combination with the nitroso compounds in the practice of the present invention are preferably of the structure:

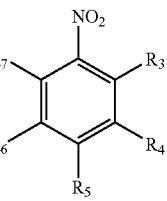

wherein $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic; and $R_8$ and $R_9$ are independently selected from the group consisting of hydrogen, alkyl, aryl, acyl, and nitroso. Preferably $R_8$ is hydrogen and $R_9$ is alkyl. Preferably, $R_3$ is hydroxyl, $R_6$ is nitro, and $R_4$ is alkyl.

The hydroxylamine compounds that can be employed in combination with the nitroso compounds in the practice of the present invention are preferably of the structure:

$$R_{100}\diagdown N \diagup R_{101}$$
$$|$$
$$OH$$

wherein $R_{100}$ and $R_{101}$ are independently selected from the group consisting of hydrogen, alkyl, alkylidene, benzylidene, aryl, benzyl, $COR_{102}$, $COOR_{102}$, $CONR_{102}R_{103}$, cyclic, heterocyclic, hydroxyalkyl, and substituted alkyl or aryl where the substituents are C, O, N, S, or P, or $R_{100}$ and $R_{101}$ can be taken together to form a ring structure of five to seven members.

The phenylenediamine compounds that can be employed in combination with the nitroso compounds in the practice of the present invention are preferably of the structure:

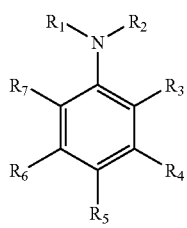

wherein $R_1$ and $R_2$ are independently selected from the group consisting of hydrogen, alkyl, aryl, acyl, hydroxyl, alkoxy, nitroso, and sulfonyl, or $R_1$ and $R_2$ can form a cyclic ring that is aryl, cycloalkyl, polyaryl, or heterocyclic;

$R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be an $NR_8(R_9)$ group; and $R_8$ and $R_9$ are independently selected from the group consisting of hydrogen, alkyl, aryl, acyl, and nitroso. Preferably, $R_1$ is hydrogen, $R_2$ is alkyl or aryl, $R_8$ is hydrogen, and $R_9$ is alkyl.

The quinone compounds that can be employed in combination with the nitroso compounds in the practice of the present invention are preferably of the structure:

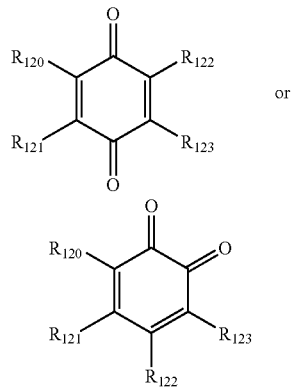

wherein $R_{120}$, $R_{121}$, $R_{122}$, and $R_{123}$ are independently selected from the group consisting of hydrogen, alkyl, aryl, cycloalkyl, sulfonyl, heterocyclic, substituted alkyl, substituted aryl, $OR_{110}$, $NR_{110}R_{111}$, $SR_{110}$, NO, $NO_2$, CN, $COR_{112}$, and halogen, or $R_{120}$ and $R_{121}$ can be taken together and/or $R_{122}$ and $R_{123}$ can be taken together to form one or two ring structures, respectively, either of which can be of five to seven members;

$R_{110}$ and $R_{111}$ are independently selected from the group consisting of hydrogen, alkyl, aryl, benzyl, cyclic, heterocyclic, substituted alkyl or aryl where the substituents are C, O, N, S, or P, and $COR_{102}$, or $R_{110}$ and $R_{111}$ can be taken together to form a ring structure of five to seven members;

$R_{112}$ is $R_{102}$, $OR_{102}$, or $NR_{102}R_{103}$; and $R_{102}$ and $R_{103}$ are independently selected from the group consisting of hydrogen, alkyl, aryl, benzyl, cyclic, heterocyclic, and substituted alkyl or aryl where the substituents are C, O, N, S, or P, or $R_{102}$ and $R_{103}$ can be taken together to form a ring structure of five to seven members.

The hydroquinone compounds that can be employed in combination with the nitroso compounds in the practice of the present invention are preferably of the structure:

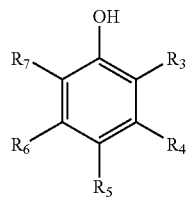

wherein $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be an OH group; and $R_8$ and $R_9$ are independently selected from the group consisting of hydrogen, alkyl, aryl, acyl, and nitroso. Preferably, either $R_5$ is OH and $R_3$ and $R_6$ are alkyl or $R_3$ is OH and $R_5$ is alkyl.

In the foregoing, alkyl (or substituted alkyl) groups, or the alkyl moieties of alkoxy groups, preferably contain one to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that the alkyl (or substituted alkyl) groups be of one to five carbon atoms (e.g., methyl, ethyl, propyl, butyl, pentyl, and isomers thereof). Substituents on the substituted alkyl groups can be any moiety that will not interfere with the functions of the compounds. Aryl groups are preferably of from six to 10 carbon atoms, e.g., phenyl or naphthyl, which, in addition, may be substituted with non-interfering substituents, e.g., lower alkyl groups, halogens, and the like.

The effective amount of nitroso compound(s), alone or in combination with a nitroxyl, and/or nitroaromatic, and/or quinone alkide, and/or quinone, and/or hydroquinone, and/or hydroxylamine, and/or phenylenediamine compound(s), is typically about 1 to 2,000 ppm, based on the weight of the ethylenically unsaturated monomer, although amounts outside this range may be appropriate depending upon the conditions of use. The amount is preferably in the range of from about 5 to about 1,000 ppm, based on the weight of the ethylenically unsaturated monomer.

The air or oxygen used in the practice of the present invention the amount is typically about 1 to 2,000 ppm, based on the weight of the ethylenically unsaturated monomer, although amounts outside this range may be appropriate depending upon the conditions of use. The amount is preferably in the range of from about 1 to about 1,000 ppm, based on the weight of the ethylenically unsaturated monomer.

Preferred embodiments of the instant invention comprise a process wherein a mixture is used that is from 1 to 99 percent by weight of at least one nitroso compound and 99 to 1 percent by weight of at least one additional compound. A more preferred mixture comprises from 5 to 75 percent by weight of at least one nitroso compound and 95 to 25 percent by weight of at least one additional compound. A still more preferred mixture comprises from 5 to 50 percent by weight of at least one nitroso compound and 95 to 50 percent by weight of at least one additional compound.

The ethylenically unsaturated monomer, the premature polymerization of which is an object of the present invention, can be any such monomer for which unintended polymerization during its manufacture, storage, and/or distribution is a problem. Among those monomers that will benefit from the practice of the present invention are: styrene, (α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, isoprene, and the like.

The ethylenically unsaturated monomers will not necessarily be stabilized indefinitely by the presence of the inhibitor blend, especially when the monomers are heated as in distillation, but they can be considered to be stabilized as long as there is a measurable increase in the time for which they can be heated before the onset of polymerization in a static system and/or the amount of polymer made at constant temperature remains constant over time in a dynamic system.

Those skilled in the art will understand that, if desired, additional free radical scavengers can be included in the stabilized compositions. For example, air or $O_2$, as disclosed in U.S. Pat. Nos. 5,545,782 and 5,545,786, can be added, as can the dihetero-substituted benzene compounds having at least one transferable hydrogen, e.g., a quinone derivative such as the mono-methyl-ether of hydroquinone disclosed in European Patent Application 0 765 856 A1, and other inhibitors well-known to those skilled in the art. The disclosures of the foregoing are incorporated herein by reference in their entirety.

The composition(s) employed in the practice of the present invention can be introduced into the monomer to be protected by any conventional method. It can be added as a concentrated solution in suitable solvents just upstream from the point of desired application by any suitable means. For example, the individual components can be injected separately or in combination to the monomer feed tank prior to injection into a distillation train. The individual components can also be injected separately into the distillation train along with the incoming feed or through separate entry points, provided there is an efficient distribution of the compounds. Since the compounds are gradually depleted during the distillation operation, it is generally advantageous to maintain the appropriate amount thereof in the distillation apparatus by replenishing them during the course of the distillation process. Additions can be done either on a generally continuous basis or intermittently, in order to maintain the concentration of the various components above a minimum required level.

The advantages and the important features of the present invention will be more apparent from the following examples.

EXAMPLES

Preparation of Inhibitor Solution

T-Butylcatechol (TBC) is removed from commercially available styrene by distillation from $CaH_2$. The desired amount of inhibitor(s) is added to the TBC-free styrene directly, together with inert polystyrene standard (Mn from 2,000,000,500 ppm wt %), as internal standard.

Procedure for GPC Schlenk Test Under Nitrogen

To a 100 mL Schlenk flask with magnetic stirbar and septum, was added 20 mL of styrene solution with the desired amount of inhibitors. The flask was connected to a double manifold and degassed by three freeze-pump-thaw cycles to remove all oxygen and allow warming to room temperature before being placed in a pre-heated oil bath (116° C.) to heat under $N_2$. At various time intervals, 0.2 mL of solution was taken via a gas-tight syringe for Gel Permeation Chromatography (GPC) analysis. The reaction was typically stopped when the solution became too viscous to take samples via syringe and the last sample was taken directly from the flask after the flask was cooled down to room temperature and opened to air.

The above procedure is carried out to provide the following data.

TABLE

| Inhibitor system | Appearance, Polymer Make (wt %), and $M_w$ | | | | | |
|---|---|---|---|---|---|---|
| 500 ppm | 3 hr | 8 hr | 16 hr | 24 hr | 48 hr | 72 hr |
| 2NNP | Oily | Oily | Oily | Oily | Oily 22.1% | Viscous |
|  | 0.3% | 2.2% | 6.1% | 10.1% | 36,000 | 29.4% |
|  | 5,000 | 26,000 | 35,000 | 36,000 |  | 37,000 |
| DNBP | Oily | Oily | Very Viscous | Gummy |  |  |
|  | 0.7% | 2.7% | 23.8% | n.a. | n.a. | n.a. |
|  | 16,000 | 26,000 | 162,000 |  |  |  |
| SFR | Oily | Oily | Very Viscous | Gummy |  |  |
|  | 1.6% | 6.3% | 21.7% | 62.5% | n.a. | n.a. |
|  | 22,600 | 42,000 | 76,000 | 123,000 |  |  |
| QE | Oily | Viscous | Gummy |  |  |  |
|  | 0.31% | 9.2% | 40% | n.a. | n.a. | n.a. |
|  | 6,800 | 224,000 | 413,000 |  |  |  |
| XTR | Oily | Very viscous |  |  |  |  |
|  | 1.4% | 18.5% | n.a. | n.a. | n.a. | n.a. |
|  | 172,000 | 247,000 |  |  |  |  |
| 2,6-di-tertbutyl-4-nitrosophenol (75% oxime form) | Very Viscous 7.5% 140,000 | n.a. | n.a. | n.a. | n.a. | n.a. |
| 2,5-di-tert-butyl quinone | Viscous 4.5% 186,000 | n.a. | n.a. | n.a. | n.a. | n.a. |
| Cyclohexanone oxime | Gummy 11.0% 540,000 | n.a. | n.a. | n.a. | n.a. | n.a. |
| BHEB | Gummy 12.2% 550,000 | n.a. | n.a. | n.a. | n.a. | n.a. |
| Pure Styrene | Gummy 12.5% 550,000 | n.a. | n.a. | n.a. | n.a. | n.a. |

The abbreviations stand for:
2NNP (2-nitroso-1-naphthol)
DNBP (2-sec-butyl-4, 6-dinitrophenol)
QE (1,5-di-tert-butyl-3-ethylidene-6-methylenecyclohexa-1, 4-diene)
SFR (4-oxo-2,2,6,6-tetramethyl-1-piperidinyloxy)
XTR (N-(1,4-dimethylpentyl)-N-(4-nitrosophenyl)amine)
BHEB (butylatedhydroxyethylbenzene)

The above data show that 2-nitroso-1-naphthol is superior to its para-nitrosophenol counter part and other inhibitors in preventing polymer from formation. The polymer formed has very low molecular weight (can avoid crosslinking problem), low viscosity (easy to be removed) thus can offer long-term protection for the reboiler.

In view of the many changes and modifications that can be made without departing from principles underlying the invention, reference should be made to the appended claims for an understanding of the scope of the protection to be afforded the invention.

What is claimed is:

1. A method for inhibiting and retarding the premature polymerization of ethylenically unsaturated monomers in a distillation process comprising
adding to said monomers an effective amount of a compound for inhibiting and retarding the premature polymerization of the ethylenically unsaturated monomers consisting of the structure:

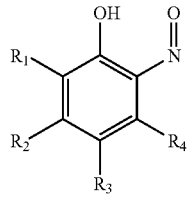

wherein $R_1$, $R_2$, $R_3$, and $R_4$ are independently selected from the group consisting of hydrogen, nitro, nitroso, halogen, COOR wherein R is hydrogen or alkyl, alkyl, and heteroatom-substituted alkyl; or adjacent groups $R_1$, $R_2$, $R_3$, and $R_4$ can be taken together to form a substituted or unsubstituted fused six-membered ring.

2. The method of claim 1 carried out in the presence of oxygen.

3. The method of claim 1 carried out in the absence of oxygen.

4. The method of claim 1 wherein the compound is 2-nitroso-naphthol.

5. The method of claim 1 wherein the compound is 1-nitroso-2-naphthol.

6. The method of claim 1 wherein the effective amount of the compound is from 1 to 2000 ppm based on the weight of the ethylenically unsaturated monomers.

7. The method of claim 1 wherein the ethylenically unsaturated monomer is selected from the group consisting of styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, and isoprene.

8. The method of claim 1 wherein the distillation process is a continuous vacuum distillation process.

* * * * *